United States Patent [19]
Worth et al.

[11] Patent Number: 4,880,016
[45] Date of Patent: Nov. 14, 1989

[54] PENILE CLAMP

[75] Inventors: Peter H. L. Worth; Ann Eaton, both of London; Peter L. Steer, Surrey, all of England

[73] Assignee: E. R. Squibb and Sons, Inc., Princeton, N.J.

[21] Appl. No.: 193,695

[22] Filed: May 13, 1988

[30] Foreign Application Priority Data

May 22, 1987 [GB] United Kingdom ................. 8712189

[51] Int. Cl.$^4$ ............................................. A61B 17/12
[52] U.S. Cl. .................................. 128/885; 128/346; 128/DIG. 25
[58] Field of Search ............... 128/346, 327, DIG. 25, 128/842, 883, 885, 887, 79

[56] References Cited

U.S. PATENT DOCUMENTS

| | | | |
|---|---|---|---|
| 678,943 | 7/1901 | Davis | 128/346 |
| 2,533,924 | 12/1950 | Foley | 128/346 |
| 2,756,753 | 7/1956 | Means | 128/346 |
| 3,147,754 | 9/1964 | Koessler | 128/346 |
| 3,155,096 | 11/1964 | Outwin | 128/346 |
| 3,203,421 | 8/1965 | Bialick | 128/346 |
| 3,866,611 | 2/1975 | Baumrucker | 128/346 |
| 4,139,007 | 2/1979 | Diamond | 128/DIG. 25 X |
| 4,760,846 | 8/1988 | Mers Kelly et al. | 128/346 X |

FOREIGN PATENT DOCUMENTS 90463 10/1983 European Pat. Off. .

Primary Examiner—Michael H. Thaler
Attorney, Agent, or Firm—Donald J. Barrack; Robert E. Lee, Jr.

[57] ABSTRACT

A penile clamp has a flexible member for encircling the shaft of the penis. It can be tightened around the penis. The arrangement and construction of the flexible member is such that such tightening causes a localized pressure to be applied to a central portion of the underside of the penile shaft.

3 Claims, 2 Drawing Sheets

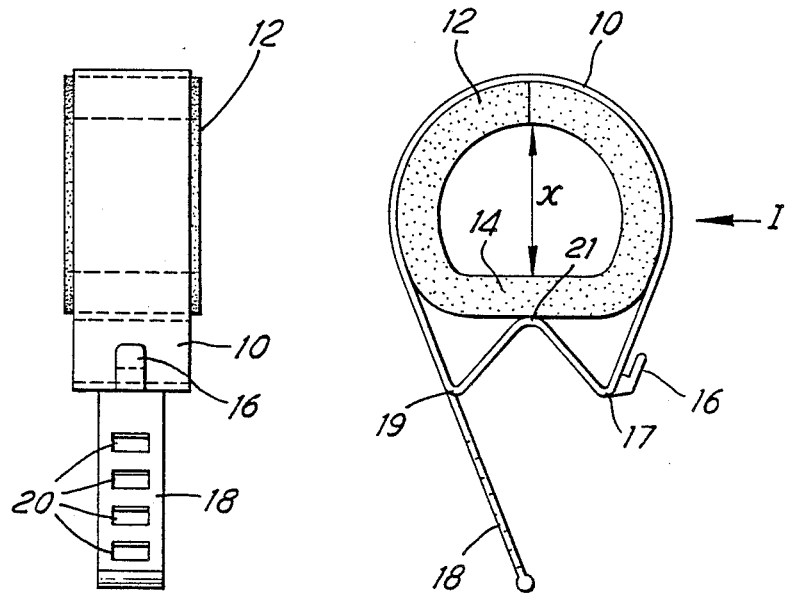

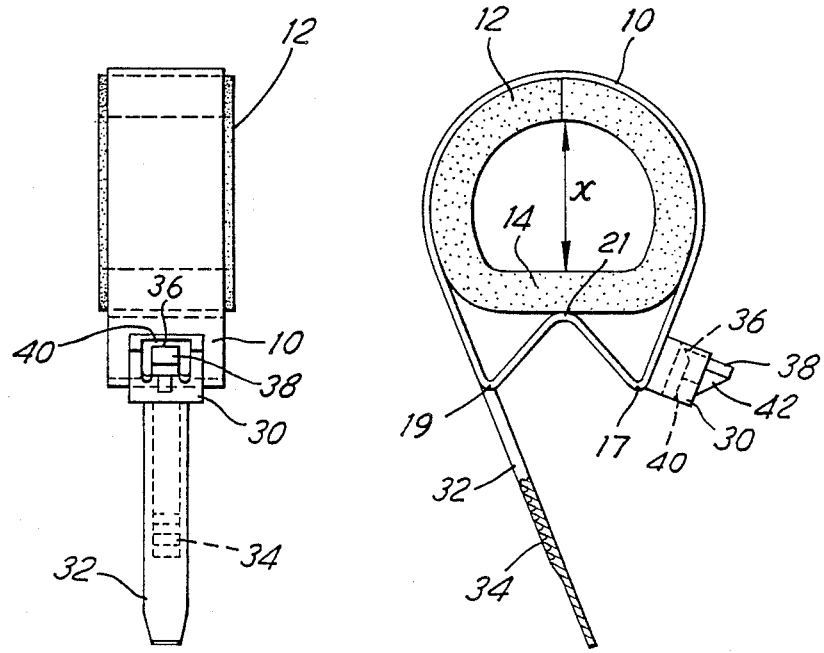

PENILE CLAMP

BACKGROUND OF THE INVENTION

The so-called "Cunningham" type of penile clamp has been in use for some years, to prevent urination by applying a clamping pressure to the penis. However, it is less than ideal in practice, chiefly because the clamping pressure is applied diffusely and not where it will be most effective. The present invention aims to provide an improved penile clamp.

Clamp type male incontinence devices are shown by Means in U.S. Pat. No. 2,756,753, Koessler in U.S. Pat. No. 3,147,754, Bialick in U.S. Pat. No. 3,203,421, Baumrucker in U.S. Pat. No. 3,866,611, and deLeur et al. in European Patent Application No. 90,463.

SUMMARY OF THE INVENTION

This invention relates to a penile clamp.

According to the present invention, a penile clamp is characterized in that it has a flexible member for encircling the shaft of the penis and which can be tightened around the penis, and in that the arrangement of the flexible member is such that the said tightening causes a localized pressure to be applied to a central portion of the underside of the penile shaft.

In a preferred embodiment of the invention, the flexible member is arranged to encircle a cushioning strip which itself encircles the penile shaft.

In an advantageous embodiment of the invention, the flexible member has thereon adjustable fastening means so that the clamp can be attached to the penis by tightening it to a selected extent.

BRIEF DESCRIPTION OF THE DRAWINGS

The invention will be better understood from the following non-limiting description of two examples thereof given with references to the accompanying drawings in which:

FIG. 1 is a side elevation view of one example of a penile clamp according to the invention looking in the direction of the arrow I in FIG. 2;

FIG. 2 is a front elevation view of the penile clamp shown in FIG. 1;

FIG. 3 is a side elevation view of a second example of penile clamp according to the invention, and FIG. 4 is a front elevation view of the penile clamp of FIG. 3.

DETAILED DESCRIPTION OF THE INVENTION

The illustrated penile clamp is intended for application to the penis at the base of the shaft and includes a flexible member 10 and a cushioning member 12. The flexible member 10 may be made of a plastics such as polyethylene and the cushioning member may be a foamed plastics such as foamed polyethylene or polyurethane. Other materials however may be used. The member 12 is approximately circular for most of its periphery but has a substantially straight portion 14. The flexible member 10 has, adjacent the flat portion 14, the configuration of a 'W'. It carries a hook 16 adjacent one (17) of the apices of the 'W'. An extension 18 narrower than the member 10 projects from another apex (19) of the flexible member 10. This extension 18 is provided with a suitable number of slots 20 (typically three or four) each of which is capable of receiving the hook 16. The member 10 and extension 18 are preferably made in one piece. The hook 16 and the slotted extension 18 constitute adjustable fastening means permitting the member 10 to be tightened around the penis to a selected extent.

The third apex 21 of the 'W' is, as will be seen from FIG. 2, located substantially centrally of the straight portion 14 and when the flexible member 10 is tightened the apex 21 applies a localized pressure to a central region of the underside of the penis. In fact it is a significant advantage of the present arrangement that this localized pressure is applied precisely where it will be most effective, that is, immediately beneath the urethra. By engaging the hook 16 in a chosen one of the four slots 20, one can achieve different values of localized applied pressure, and release of the applied pressure is easily achieved. The cushioning member 12 renders the clamp comfortable to wear, but it is not essential to the invention. By suitable design of the member 10 it is possible to do without the cushioning member 12. As illustrated in FIG. 2, a bead is provided at the free end of the extension 18, to facilitate gripping, but this is not essential. The shapes of the parts 10 and 14 clearly indicate to a user the correct way of mounting the clamp on the penis, although if desired the 'W' portion of the member 10 or the portion 14 could be colored so that this could be clearly explained in operating instructions.

FIGS. 3 and 4 illustrate another example of penile clamp having a different form of tightening arrangements; the remaining parts of the clamp are similar to those of the clamp of FIGS. 1 and 2 and will not be described in detail again. The member 10 is made in one piece with a post 30 adjacent one (17) of the apices of the W, and an elongated tab 32 adjacent another apex (19) of the flexible member 10. The elongate tab 32 has a series of depressions therein which serve as ratchet teeth 34 cooperating with the detent tooth 36 on the detent 38. The post 30 has a slot 40 therethrough, through which the elongate tab 32 can be threaded. The detent tooth 36 includes a projecting portion 42 which allows a user to lift the tooth out of engagement with the tab to allow it to be removed from the slot 40. In use, the tab 32 is threaded into the slot 40 and then pulled longitudinally to tighten the clamp to the desired extent. The clamp pressure is released by using projection 42 to release the tab 32.

In either of the above examples the member 10 may for example have a width of 15-25 mm, preferably about 18 mm, thickness of 1 to 2 mm, preferably about 1.5 mm and the extension may be about 35 mm. The cushioning member may have a thickness of 5-8 mm, preferably about 6 mm, and a width of 20-27 mm, preferably about 24 mm.

The dimensions are preferably chosen such that the distance x (FIG. 2 and FIG. 4) is between about 22 to 30 mm in the untightened condition of the clamp and about 14-22 mm in the maximum tightened condition of the clamp. Of course the distance x would be smaller for clamps employed for juveniles compared to adult males so the above-indicated dimensions (which relate to a device for an average adult male) should be considered with this point in mind. The adjustment in size may be achieved by adjustment of the thickness of the cushioning member 12 or by the adjustment of the dimensions of the member 10.

Although the embodiments illustrated are particularly convenient and effective means for achieving an adjustable and localized pressure on the precise zone of the penile shaft adjacent the urethra, other mechanical arrangements could be employed to achieve this, and the present invention is hence not to be considered as limited to the employment of the particular 'W' configuration illustrated herein.

The cushioning member 12 may have a width (axial extent) of between 22 and 28 mm, preferably about 25 mm, and a thickness between about 4 and 8 mm, preferably about 6 mm.

What is claimed is:

1. A penile clamp comprising an outer flexible member that encircles an inner cushioning member, said cushioning member dimensioned to fit around a penile shaft, said cushioning member being circular for most of its periphery but with a substantially straight portion which in use contacts the underside of the penile shaft, the portion of said outer flexible member adjacent said straight portion of said cushioning member having a configuration shaped like the letter W, the middle apex of said W contacting a central portion of said straight portion of said cushioning member and the outer apices of said W having adjustable fastening means wherein a tightening of said outer flexible member draws said outer apices closer together causing a localized pressure to be applied to a central portion of the underside of the penile shaft by the middle apex of said W.

2. A clamp according to claim 1 in which the adjustable fastening means includes a hook adjacent one of the outer apices of said W that cooperates with a slotted extension member extending from the other outer apex of said W.

3. A clamp according to claim 1 in which the adjustable fastening means includes a tooth adjacent one of the outer apices of said W that cooperates with ratchet teeth extending from the other outer apex of said W.

* * * * *